United States Patent
Tekulve

(10) Patent No.: US 9,974,544 B2
(45) Date of Patent: May 22, 2018

(54) OCCLUDING DEVICE AND METHOD OF MANUFACTURING OCCLUDING DEVICES

(71) Applicant: COOK MEDICAL TECHNOLOGIES LLC, Bloomington, IN (US)

(72) Inventor: Kurt Tekulve, Ellettsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 37 days.

(21) Appl. No.: 14/886,461

(22) Filed: Oct. 19, 2015

(65) Prior Publication Data

US 2016/0038148 A1      Feb. 11, 2016

Related U.S. Application Data

(62) Division of application No. 13/799,591, filed on Mar. 13, 2013, now Pat. No. 9,192,389.

(51) Int. Cl.
*A61B 17/12* (2006.01)
*A61B 17/00* (2006.01)

(52) U.S. Cl.
CPC .... *A61B 17/1215* (2013.01); *A61B 17/12109* (2013.01); *A61B 2017/00526* (2013.01); *A61B 2017/00862* (2013.01); *A61B 2017/00951* (2013.01); *Y10T 156/10* (2015.01)

(58) Field of Classification Search
CPC ........... A61F 2/06; A61M 29/00; A61B 17/00
USPC ................. 623/1.1–1.37; 604/264, 523–527; 606/191–200
See application file for complete search history.

(56) References Cited

U.S. PATENT DOCUMENTS

| | | |
|---|---|---|
| 5,658,308 A | 8/1997 | Snyder |
| 5,976,162 A | 11/1999 | Doan et al. |
| 6,187,027 B1 | 2/2001 | Mariant et al. |
| 6,358,228 B1 | 3/2002 | Tubman et al. |
| 7,744,583 B2 | 6/2010 | Seifert et al. |
| 2004/0098023 A1 | 5/2004 | Lee et al. |
| 2006/0116711 A1 | 6/2006 | Elliott et al. |
| 2007/0142859 A1 | 6/2007 | Buiser et al. |
| 2007/0239194 A1 | 10/2007 | Tran et al. |
| 2008/0103585 A1 | 5/2008 | Monstadt et al. |
| 2008/0221554 A1 | 9/2008 | O'Connor et al. |
| 2012/0226304 A1 | 9/2012 | Ryan et al. |

*Primary Examiner* — Yashita Sharma
(74) *Attorney, Agent, or Firm* — Brinks Gilson & Lione

(57) ABSTRACT

An occluding device for occlusion of fluid flow through a lumen of a body vessel manufactured by wedging fibers between adjacent coil windings of a primary coil so that the fibers extend generally radially across the primary coil body between the primary coil windings and outward therefrom. An elongated adhesive is inserted applicator into the primary coil lumen and subsequently proximally withdrawn while simultaneously depositing along the primary coil windings. The fibers and the adhesive are placed in overlapping locations so that the fibers extend through the adhesive. The fibers are thus blocked from slipping along their length relative to the coil body by the adhesive adhering to the fibers inside the primary coil lumen. The adhesive extends radially outward from the coil lumen no farther than the outer primary coil radius. The adhesive adheres to the fibers and may or may not adhere with the primary coil windings.

16 Claims, 4 Drawing Sheets

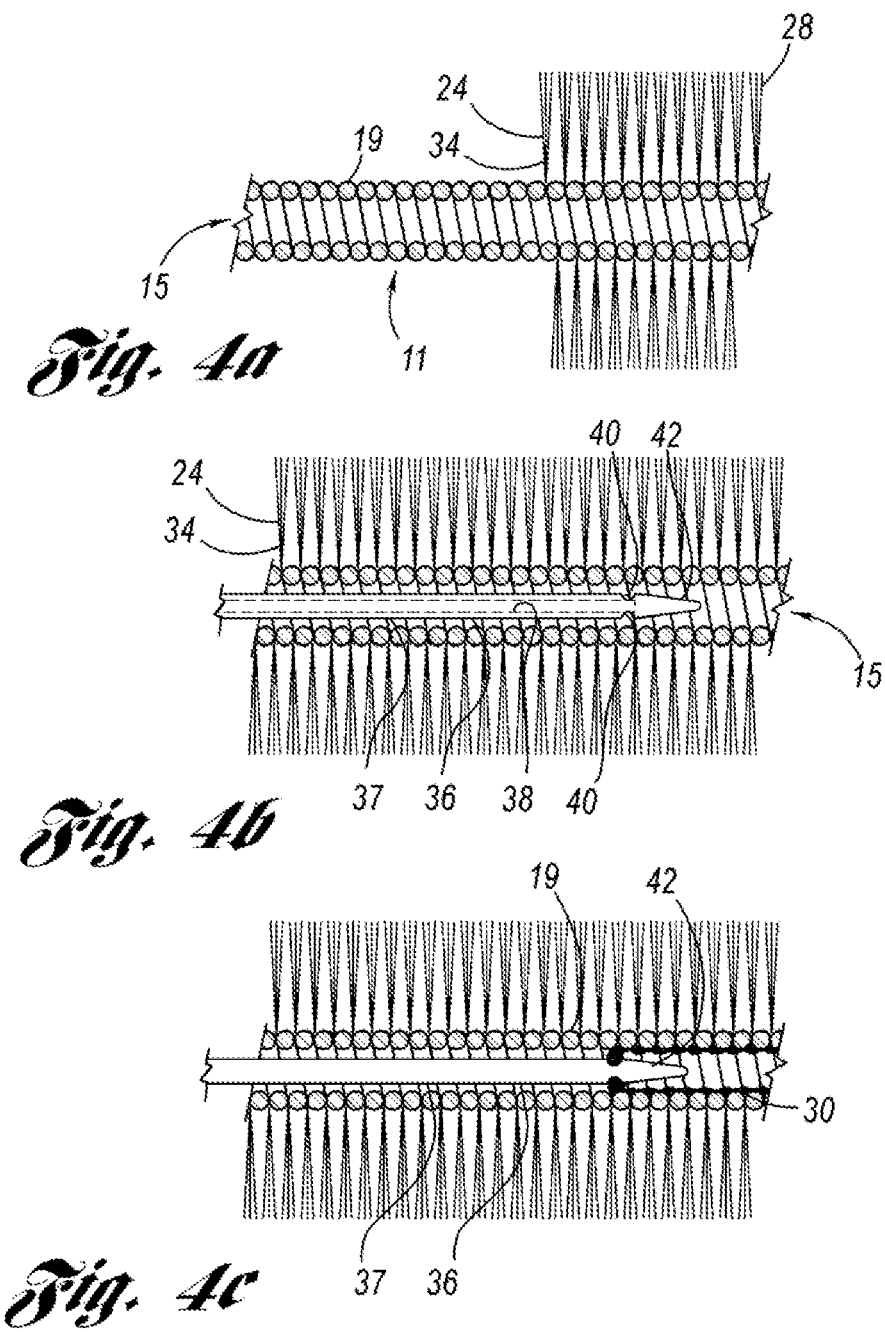

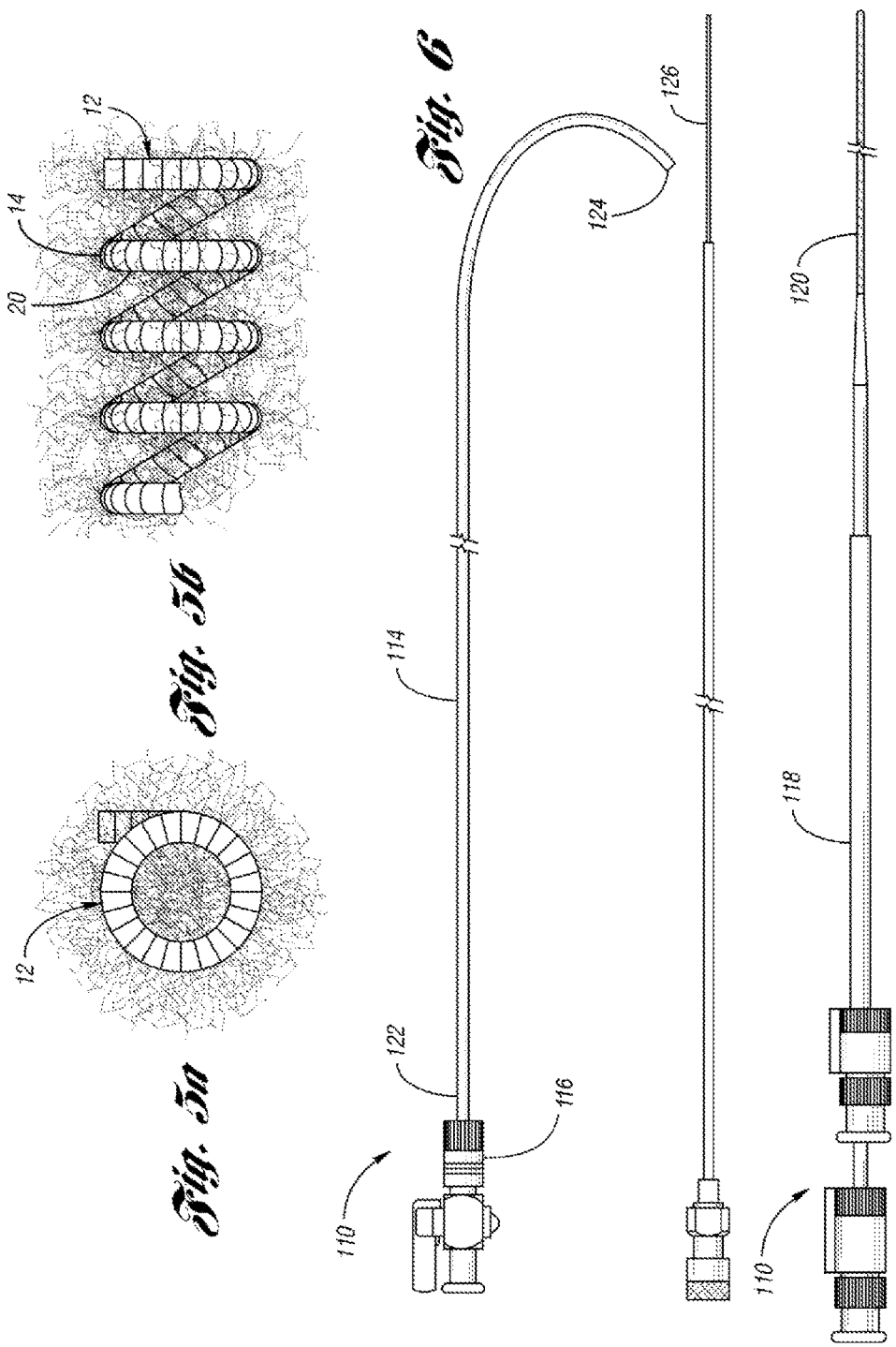

OCCLUDING DEVICE AND METHOD OF MANUFACTURING OCCLUDING DEVICES

CROSS-REFERENCE TO RELATED APPLICATIONS

This application is a divisional application of U.S. patent application Ser. No. 13/799,591, filed Mar. 13, 2013, the entire contents of which is incorporated herein by reference.

TECHNICAL FIELD

The present invention relates to medical devices. More particularly, the invention relates to occluding devices and methods of manufacturing occluding devices.

BACKGROUND

Fibered coils have been used as a primary occluding device for treatment of various arteriovenous malformations (AVM) and varicoceles, as well as for many other arteriovenous abnormalities in the body. Occluding devices are also used to repair abnormal shunts between arteries and veins, prevent or reduce blood flow to tumors, stop hemorrhaging as a result of trauma, and stabilize aneurysms to prevent rupture. Pushable and fluid-deliverable fibered coils may be configured in a variety of sizes with varying diameters and may be made of several different materials including stainless steel and platinum.

Some fibered coils have strands of fiber wedged between the coil windings. Upon deployment in a body vessel for occlusion, such coils are bent, thus locally increasing the space between the coil windings.

SUMMARY

The present invention provides an improved occluding device and an improved method of manufacturing such an occluding device.

According to a first aspect of the invention, an occluding device for occlusion of fluid flow through a lumen of a body vessel comprises a primary coil having primary coil windings forming a primary coil body with an outer primary coil radius and a primary coil lumen; and fibers attached to the primary coil, the fibers having a length extending generally radially across the primary coil body between the primary coil windings and outward therefrom, the fibers being blocked from slipping along their length relative to the coil body by an adhesive adhering to the fibers inside the primary coil lumen, the adhesive extending radially outward from the coil lumen no farther than the outer primary coil radius. Thus, the fibers are secured inside the primary coil windings without increasing the diameter of the primary coil during delivery.

According to one embodiment of the invention, the adhesive is made of a material that does not form a bond with the primary coil windings. The thus chosen adhesive locks the fibers inside the primary coil without affecting the flexibility of the primary coil. Alternatively or additionally, the adhesive may be made of a durably elastic material.

According to another embodiment of the invention, the adhesive may joins a plurality of fiber strands into a fiber bundle. Out of the plurality of fiber strands, two or more fiber strands may extend across the primary coil body between different primary coil windings, thus providing an additional safeguard against dislodging of fiber strands. Even if the primary coil were to break in one location, the fiber bundle would still be secured by the fiber strands extending between different coil windings.

According to a further aspect of the invention, the adhesive may thicken the fibers inside the primary coil lumen to a thickness greater than a distance between adjacent primary coil windings and thereby lock the fibers relative to the primary coil. Preferably, the thickness is greater than the distance between adjacent coil windings when the primary coil is in a bent configuration. For example, if the primary coil has a relaxed shape that is curled into a secondary coil with a series of secondary loops, the thickness of the adhesive-thickened fibers is preferably greater than the distance between the adjacent coil windings when the primary coil is in its relaxed shape.

According to yet another aspect of the invention, the adhesive is made of a material that forms bonds with both the fibers and the primary coil windings. Preferably, the adhesive material is then chosen from durably elastic materials.

According to one aspect of the invention, an occluding device for occlusion of fluid flow through a lumen of a body vessel is manufactured by a method comprising the steps of providing a primary coil having primary coil windings forming a primary coil body with an outer primary coil radius and a primary coil lumen; wedging fibers between adjacent coil windings so that the fibers extend generally radially across the primary coil body between the primary coil windings and outward therefrom; distally inserting an elongated adhesive applicator into the primary coil lumen; proximally withdrawing the adhesive applicator while simultaneously depositing along the primary coil windings; and wherein the fibers and the adhesive are placed in overlapping locations so that the fibers extend through the adhesive. In the course of performing the method, the fibers may be wedged between the adjacent coil windings before the adhesive is deposited, or afterwards.

In one embodiment of the invention, the elongated adhesive applicator is a wire guide.

According to a further aspect of the invention, the wire guide may be hollow with a longitudinal channel extending from a proximal end to at least one opening near a distal end. For example, the at least one opening may be formed by two radial openings opposite each other.

According to yet another aspect of the invention, the at least one opening may be proximally adjacent to a tapered or rounded distal tip. Preferably, the tapered or rounded distal tip has a length of at most about 1 cm.

According to an alternative aspect of the invention, the elongated adhesive applicator has an outer surface, and the method comprises the further step of applying adhesive to the outer surface prior to inserting the adhesive applicator into the primary coil lumen.

Further details and benefits of the invention become apparent from the following description of various embodiments shown in the attached drawings. The drawings are provided for purely illustrative purposes and are not intended to limit the scope of the present invention.

BRIEF DESCRIPTION OF THE DRAWINGS

In the drawings,

FIG. 2b is a cross-sectional view of the primary coil in FIG. 2a;

FIG. 3b illustrates a second step of the method of FIG. 3a;

FIG. 4a illustrates a first step of a second embodiment of a method of assembling the occluding device of FIG. 2;

FIG. 4b illustrates a second step of the method of FIG. 4a;

FIG. 4c illustrates a third step of the method of FIGS. 4a and 4b;

FIG. 5a is a cross-sectional view of the occluding device of FIG. 1a taken along line 5a-5a;

FIG. 5b is an enlarged view of the occluding device in area 5b of FIG. 1a; and

FIG. 6 is an exploded view of an embolization kit for one embodiment of the occluding device of the present invention;

DETAILED DESCRIPTION OF THE DRAWINGS

The following provides a detailed description of currently preferred embodiments of the present invention. The description is not intended to limit the invention in any manner, but rather serves to enable those skilled in the art to make and use the invention.

The present invention generally provides an occluding device used for transcatheter embolization. The occluding device is preferably used to occlude fluid flow through a lumen of a body vessel such as for an occlusion of an arteriovenous malformation (AVM). The occluding device comprises a primary coil having a relatively low initial tension. The primary coil may be formed in a helical shape to define a secondary coil. Preferably, the primary coil 11 assumes the shape of the secondary coil 12 in a relaxed state, i.e. without the influence of any external forces. The occluding device may be made of any material suitable for occluding devices that is preferably detectable with customary imaging methods, for example platinum for its radiopacity.

The occluding device preferably includes fibers wedged or attached between loops of the primary coil and extending therefrom. When the occluding device is deployed in a lumen of a body vessel, the fibers help to occlude fluid flow through the lumen of the body vessel.

The occluding device also may be used for treatment of renal AVM, pulmonary AVM, vascular tumors, low-flow fistulas, trauma related hemorrhages, and visceral vasculature defects including varicoceles, aneurysms, and selected telangiectasias. For example, treatment of visceral vasculature defects may include but are not limited to embolotherapy on gastroduodenal hemorrhages, hepatic aneurysms, celiac aneurysms, internal iliac aneurysms, and internal spermatic varicoceles.

Figure 1A:
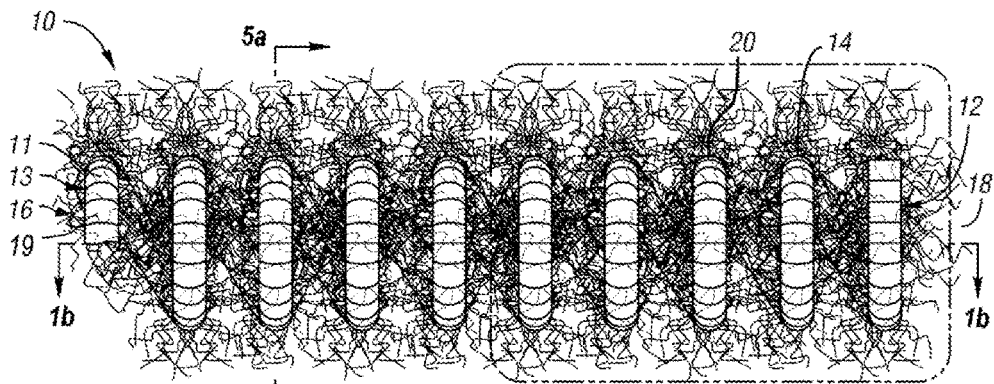
FIG. 1a is a side view of an occluding device in accordance with one embodiment of the present invention.

FIG. 1a illustrates an occluding device 10 for occlusion of fluid flow through a lumen of a body vessel in accordance with one embodiment of the present invention. The occluding device shown in FIGS. 1a through 2b, 5a, and 5b comprises a primary coil 11 formed in a secondary coil 12. The primary coil 11 is formed to define a primary body 13 defined by primary windings 19 that are arranged adjacent to each other with minimal spacing and that surround a primary lumen 15. The primary body 13 may be further shaped by a coil winding machine into a helical shape to define a secondary coil 12. The secondary coil 12 includes a series of secondary loops 20 of a secondary body 14 having a first end 16 and a second end 18. The series of secondary loops 20 define a cross-sectional lumen formed axially along the secondary coil 12 as seen in FIG. 5a. Preferably, the occluding device 10 further includes fibers 24 attached to the primary windings 19 of the primary coil 11.

Preferably, the primary coil 11 comprises platinum or any other suitable metal, composition, or alloy having between about 50,000 and 350,000 pounds per square inch tensile strength. It has been determined that the tensile strength range described above provides the coil with the capability of being flexible, malleable, and folded.

The primary coil 11 may be made by any apparatus known in the art. For example, the coil may be made by any commercial coil winding machine such as a roller deflecting apparatus, a mandrel apparatus, or any other suitable means.

In this embodiment, the primary coil 11 may have a length of between about 3 to 20 centimeters. As shown in FIG. 5a, the secondary coil 12 may have an outer diameter ranging between about 3 and 45 millimeters. For most applications, the outer diameter will not exceed about 25 millimeters. The primary coil 11 may have an outer diameter of between about 0.010 and 0.04 inch. The catheter inner diameter through which the occlusion device may be advanced ranges between about 0.014 and 0.045 inch, depending on the outer diameter of the primary coil 11.

FIGS. 1 and 5b illustrate the helical body 14 of the secondary coil 12 having a series of connected secondary loops 20 axially spaced apart by a predetermined distance. In this embodiment, the predetermined distance of up to 4 millimeters curl space. Curl space is defined as the distance between two secondary loops 20 of secondary coil 12.

Figure 1B:
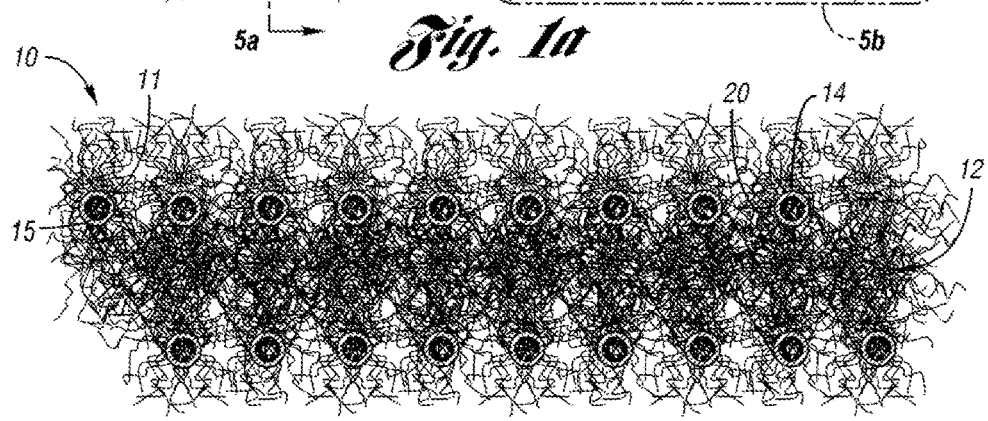
FIG. 1b is a cross-sectional view of the occluding device of FIG. 1a taken along line 1b-1b.
Figure 2A:
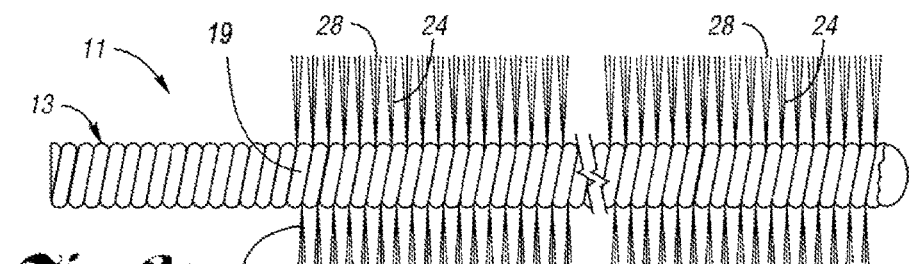
FIG. 2a is a side view of a primary coil in FIG. 1 depicting the occluding device in an uncoiled length.

As shown in FIGS. 1 and 2, the fibers 24 of the occluding device 10 are attached to the primary coil 11 and extend therefrom. The fibers 24 are spaced apart from each other and are held between the primary windings 19 of the primary coil 11. The fibers 24 include strands 28 made of a synthetic polymer such as a polyester textile fiber, e.g., DACRON™. As desired, the strands may be wedged between alternating primary windings 19, alternating double primary windings 19, or any desired configuration. The strands 28 being held spaced apart from each other along the extended length of the primary coil 11, e.g., 14 centimeters, avoid an enlarged diameter created when fibers 24 fold or bend over each other when the primary coil 11 is loaded in a catheter. As a result, an undesirable resistance is avoided when the primary coil 11 is advanced through the catheter.

Preferably, the strands 28 have a length extending generally radially across the primary body 13 between the primary windings 19 and outward from the primary coil 11. The length of the fibers 24 ranges between about 3 and about 8 millimeters. In an application the strands may be between about 5 to 6 millimeters long as desired. In this embodiment, the fibers 24 are spaced apart from each other by about 1 to 3 millimeters. Preferably, the strands 28 have an outer diameter of about 0.0005 to 0.002 inch.

Figure 2B:
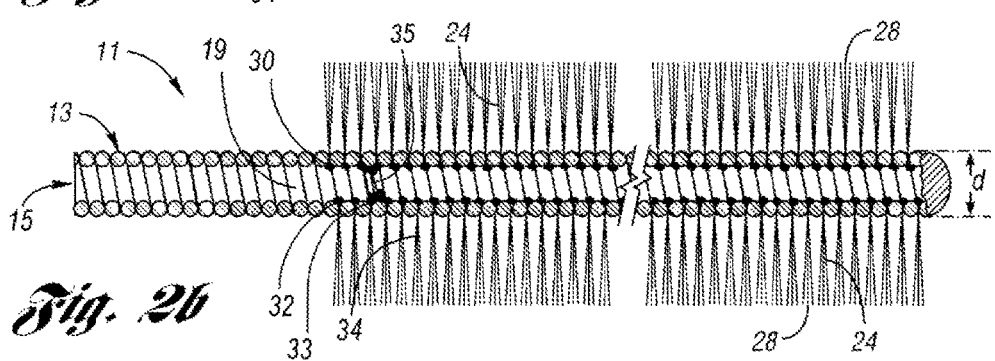

As shown in FIG. 1b and, in more detail, in FIG. 2b, the fibers 24 are blocked from slipping out of the primary body 13 along their length by an adhesive 30 adhering to the fibers inside the primary coil lumen. In the shown embodiments, the adhesive 30 forms beads 32 around the fibers 24. The adhesive 30 is generally located inside the lumen 15 of the primary coil 15. Small amounts of the adhesive 30 may extend between the primary coil windings, but an improved method of manufacturing the occluding device 10 described below ensures that the adhesive generally does not extend farther outward than the outer diameter d of the primary coil 11. Thus, the adhesive does not enlarge the diameter of the occluding device 10 and does not impede the delivery of the primary coil 11 through a catheter or a syringe.

FIG. 2b shows the adhesive beads 32 in two locations along the length of each of the fibers 24. The two locations are those inside the lumen 15 of the primary coil 11 that are adjacent to the primary windings 19. The adhesive 30 may have a high surface tension that promotes beading around the fibers 24. Alternatively, the adhesive may only be applied to one location along each fiber 24 or along the entire portion of the fiber that extends inside the primary lumen 15.

In one embodiment of the invention, the adhesive 30 is made of a material that does not form a bond with the preferably metallic primary windings 19, but with the material of the fibers 24. Preferably, the adhesive 30 is applied in a low-viscosity state that obtains a higher viscosity after the fibers 24 have been inserted between the primary windings 19. For example, the material of the adhesive 20 and of the fibers 24 may be chosen to promote cross-linking during a drying or curing process. The curing process may be facilitated by heat, light, or a chemical process over time. Alternatively, the adhesive 30 may be made of a material that forms bonds with both the fibers 24 and the primary coil windings 19.

The adhesive 30 may further be made of a durably elastic material, for example silicone. Due to the elasticity, the adhesive 30 resists breakage and chipping when the primary coil 11 is deformed before and after implantation in a body vessel. Especially if the adhesive 30 also bonds with the primary windings 19, it is also preferable that the adhesive 30 retains some elasticity to compensate for movements of the primary coil windings 19 relative to each other while the primary coil 11 is loaded into a catheter or syringe and during implantation.

As shown in FIG. 2b, the adhesive 30 may join a plurality of fiber strands 28 into a fiber bundle 34. While FIG. 2b shows fiber bundles 34 with fiber strands 28 that all extend between the same primary windings 19, alternatively, different fiber strands 28 of the same fiber bundle 35 may also extend outward between different primary windings 19 so that the fiber bundle 35 may, for example, be bifurcated or trifurcated through the primary windings 19. Larger beads 33 of adhesive may be formed to adhere to the strands 28 of the split fiber bundle 35. Although only one of the split fiber bundles 35 is shown in FIG. 2b, several or all fiber bundles of the occluding device may be split among primary windings 19. Thus, even if the primary coil 11 were to be damaged in one location, the fiber bundle 35 would still be secured by fiber strands 28 extending between primary windings 19 unaffected by the damage.

Preferably, the adhesive thickens the fibers 24 inside the primary coil lumen 15 to a thickness that is greater than the distance between the adjacent primary coil windings 19. While the primary coil 11 is usually tightly wound so that no or only minimal spaces are present between the primary windings 19 when the primary coil 11 is straightened absent an expanding force, the spaces increase when the primary coil 11 is curled into the secondary coil 12 or when the primary coil 11 is bent during implantation in the body vessel. Preferably, the adhesive, in the form of the beads 32 or other shapes, thickens the fibers to a thickness that amounts to at least the space between the primary windings 19 when the primary coil 11 assumes a bent shape, particularly the curled shape of the secondary coil 12.

FIGS. 3a through 3d illustrate a first example of a method of assembling the occluding device 10. An elongated adhesive applicator 36 is inserted into the primary coil lumen from one axial side and through the primary lumen 15 to the other coaxial end of the primary coil 11. For example, the adhesive applicator 36 may be a wire guide 37.

In one embodiment of the invention, the wire guide 37 is hollow with a longitudinal channel 38 extending from a proximal end to openings 40 near a distal end. In the embodiment of FIG. 3, two radial openings 40 are provided opposite each other. It is, however well within the scope of the present invention to provide only one opening 40, for example at the distal end of the wire guide 37, or more than two openings 40. The openings may be distributed around the circumference of the wire guide. Also, the openings 40 may be axially offset from each other to allow for larger openings 40 than if all openings 40 were all placed side by side in a single axial location the wire guide.

If the opening or openings 40 are radial openings, the wire guide 37 may have a rounded or tapered distal tip 42 facilitating the insertion of the wire guide 37 into the primary coil 11 without damage to the primary windings 19. In the example shown, the distal tip 42 is rounded, but it may additionally be tapered. The rounded tip may even make it possible to insert the wire guide into the primary coil 11 without first straightening the primary coil 11. The primary coil 11 can easily slip past the rounded tip 42 without damage or plastic deformation, and the rounded tip reduces the risk that the distal end of the wire guide 37 could get caught on any of the primary windings 19.

The tapered or rounded distal tip 42 does not need to be very long to facilitate threading the primary coil onto the wire guide 37. The distal tip 42 may have a length of up to about 1 cm. While such a short length of the distal tip 42 is preferred, greater lengths are still within the scope of the present invention.

Instead of a hollow adhesive applicator 36, a solid elongated adhesive applicator may be used for applying the adhesive.

Once the adhesive applicator 36 is inserted into the primary lumen 15, the adhesive applicator 26 is slowly withdrawn while the adhesive 30 is simultaneously applied to the primary coil windings 19 inside the primary lumen 15.

When a solid applicator 36 is used to deposit the adhesive, the adhesive 30 may be applied to the outer surface of the adhesive applicator 36 prior to inserting the adhesive applicator 36 into the primary coil lumen 15. This method of depositing the adhesive 30 is mostly suited for relatively short primary coils 11 because the adhesive 30 may be depleted over only a short axial distance along the primary coil. To double the axial length, in which the adhesive is deposited, the solid adhesive applicator 36 may also be inserted into the lumen and withdrawn from the opposite end of the primary coil 11.

Figure 3A:
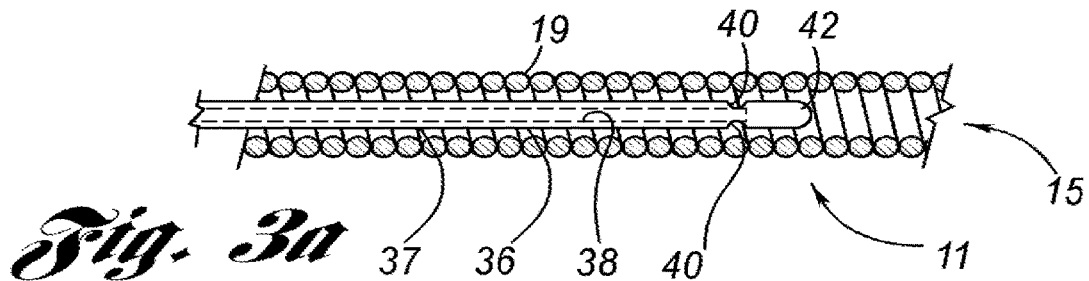
FIG. 3a illustrates a first step of a first embodiment of a method of assembling the occluding device of FIG. 2.
Figure 3B:
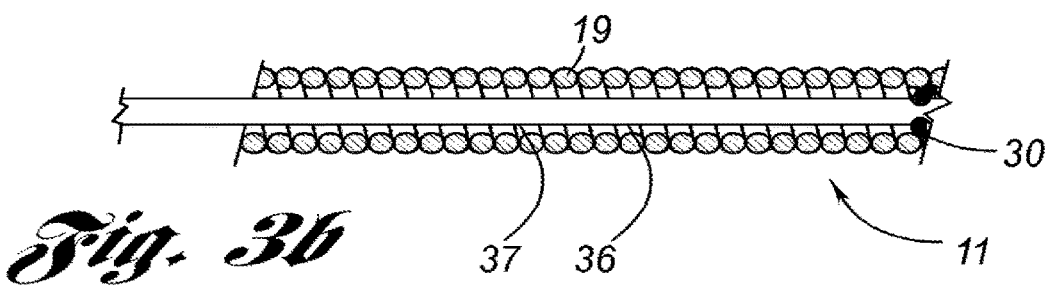
Figure 3C:
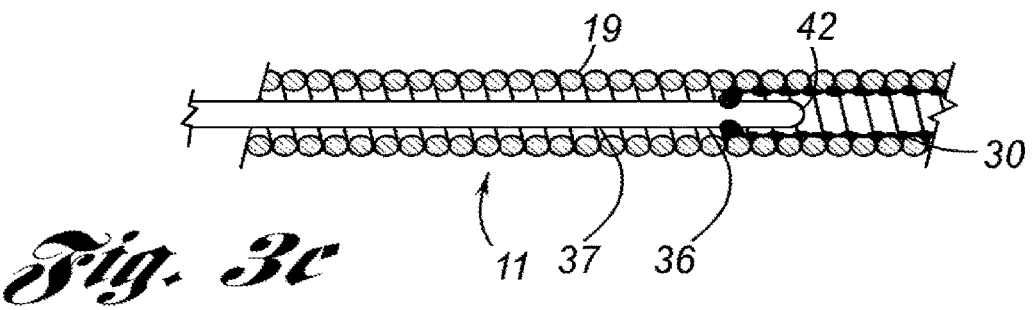
FIG. 3c illustrates a third step of the method of FIGS. 3a and 3b.

Especially for longer primary coil 11, the hollow guide wire 37 as shown in FIGS. 3a through 3c is better suited for an even axial distribution of the adhesive 30. While the guide wire 37 is withdrawn from the primary lumen 15, the adhesive 30 is pressed from the proximal end of the guide wire 37 through the longitudinal channel and out of the openings 40 onto the inside surfaces of the primary windings 19. The two radial openings 40 of the shown embodiments created to longitudinal lines of adhesive 30 that are circumferentially offset by about 180°. Thus the adhesive is deposited in two lines extending opposite to each other along the inside of the primary lumen 15. Alternatively, a single distal opening 40 in the guide wire 37 might be used to substantially fill out the primary lumen 15 with the adhesive 30, or a greater number of radial openings 40 may be used to create more than two longitudinal lines of adhesive 30 along the inside of the primary lumen 15.

Figure 3D:
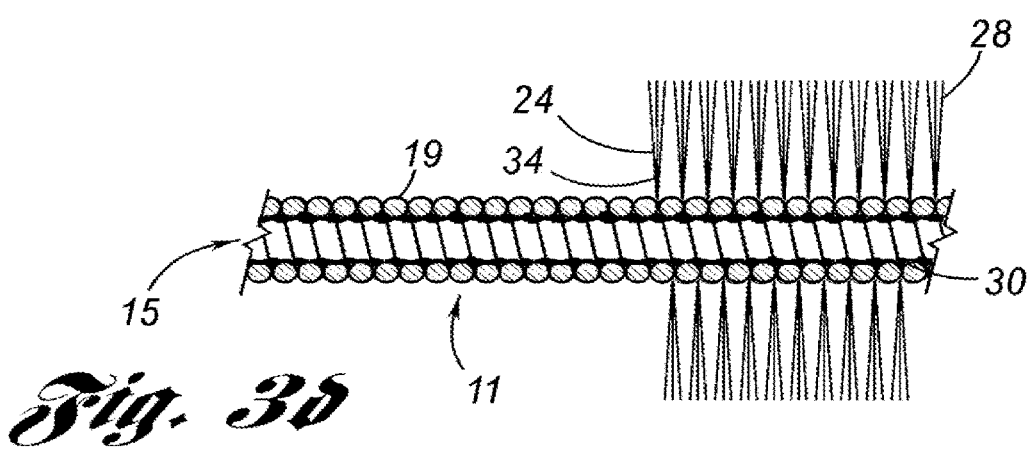
FIG. 3d illustrates a fourth step of the method of FIGS. 3a through 3c.

As shown in FIG. 3d, after the adhesive 30 has been deposited inside the primary lumen 15, the fibers 24 may be wedged between adjacent primary coil windings 19 in angular locations where the adhesive has been deposited. For example, as the lines of adhesive 30 are shown to be located at the top and at the bottom of the primary lumen 15, the fibers 24 may be inserted in a generally vertical orientation. In FIG. 3d, for example, the fibers may be inserted between two adjacent primary coil windings 19 from behind, i.e. from the background of the drawing toward the foreground of the drawing. As a result, the fibers 24 extend generally radially across the primary body 13 between the primary coil windings 19 and outward therefrom. Because the fibers 24 were inserted between the primary windings 19 in a direction generally perpendicular to the length of the fibers 24, none of the adhesive 30 comes into contact with any portions of the fibers 24 that extend outward from the primary body 13. This process ensures that the adhesive remains mostly inside the primary lumen and does not enlarge the outer diameter d of the primary coil 11.

In a second embodiment of the method of assembling the occluding device 10, the step of FIG. 3d is performed first, before any adhesive is deposited in the primary coil 11, as illustrated in FIGS. 4a through 4c. After all the fibers 24 have been placed in their positions between the primary windings 19 according to FIG. 4a, the adhesive applicator 36 with a preferably tapered tip 42 is inserted into the primary lumen 15, according to FIG. 4b, and deposits the adhesive 30 in the primary lumen 15. Because the fibers 24 are already present, the tapered tip 42 has a distal end that is preferably narrow enough to form a path past the fibers 24 and that does not pull the fibers 24 into the primary lumen. Thus, the steps of FIGS. 4b and 4c of depositing the adhesive 30 inside the primary lumen 15 may be performed after the step shown in FIG. 4a. In this second embodiment of the method according to FIG. 4, the fibers 24 may be pulled lengthwise between the primary windings 19, i. e. along the length of the fibers 24, because no adhesive is present inside the primary lumen 15. Thus, even if a fiber portion is pulled from the inside of the primary lumen 15 to the outside, that portion of the fibers 24 has not come into contact with any of the adhesive 30 yet so that the adhesive 30 does not increase the outer diameter d of the primary coil 11. As mentioned in connection with the method of FIG. 3, this second embodiment may also be performed with an applicator having different arrangements of the openings 40, such as a single distal or radial opening or a plurality of openings distributed around the circumference that may additionally or alternatively be axially offset from each other.

Further, while not shown, it is evident that the adhesive may also be applied in an amount filling out the entire lumen of the primary coil 11 by either one of the methods of FIGS. 3 and 4.

During deployment of the occluding device 10, the primary coil 11 may be folded across the lumen of a body vessel to be occluded. When the device 10 is deployed from a catheter, a low inherent tension of the primary coil provides the primary coil the capability of being folded across the lumen of a body vessel for cross-sectional occlusion. In this embodiment, when the primary coil is folded with the strands 28, the occluding device 10 is in a "packed" or "nested" state a length of about 5% or more of the original length of the primary coil 11 as generally known from the prior art. When packed, the occluding device 10 provides a relatively tightly nested, dense mass that effectively occludes fluid flow though a lumen of a body vessel.

FIG. 6 depicts a body vessel embolization kit 110 which implements the occluding device in accordance with one embodiment of the present invention. As shown, the kit 110 includes a microcatheter 114 defining a catheter lumen and preferably made from a soft, flexible material such as silicone or any other suitable material. Generally, the microcatheter 114 has a proximal end 122, a distal end 124, and a plastic adapter or hub 116 to receive apparatus to be advanced therethrough. In this embodiment, the inside diameter of the microcatheter 114 may range between 0.014 and 0.027 inch. The kit 110 further includes a guide wire 120 which provides the guide catheter 118 a path during insertion of the guide catheter 118 within a body vessel. The size of the wire guide 120 is based on the inside diameter of the guide catheter 118.

In this embodiment, the guide catheter or sheath 118 of the kit 110 is made of polytetrafluoroethylene (PTFE) for percutaneously introducing the microcatheter 114 in a body vessel. Of course, any other suitable material may be used without falling beyond the scope or spirit of the present invention. The guide catheter 118 may have a size of about 4-French to 8-French and allows the microcatheter 114 to be inserted therethrough to a desired location in the body vessel. The guide catheter 118 receives the microcatheter 114 and provides stability of the microcatheter 114 at a desired location of the body vessel. For example, the guide catheter 118 may stay stationary within a common visceral artery, e.g., a common hepatic artery, and add stability to the microcatheter 114 as the microcatheter is advanced through the guide catheter to a point of occlusion in a connecting artery, e.g., the left or right hepatic artery.

When the distal end 124 of the microcatheter 114 is at the point of occlusion in the body vessel, the occluding device is loaded at the proximal end 122 of the microcatheter 114 and is advanced through the microcatheter for deployment through the distal end 124. In this embodiment, a push wire 126 is used to mechanically advance or push the occluding device through the microcatheter 114. The size of the push wire used depends on the diameters of the microcatheter.

It is to be understood that the body vessel embolization kit 110 described above is merely one example of a kit that may be used to deploy the occluding device in a body vessel. Of course, other kits, assemblies, and systems may be used to deploy any embodiment of the occluding device without falling beyond the scope or spirit of the present invention.

The occluding device may be deployed in a body vessel by a push embolization method or a squirt embolization method in accordance with the present invention.

While the present invention has been described in terms of preferred embodiments, it will be understood, of course, that the invention is not limited thereto since modifications may be made to those skilled in the art, particularly in light of the foregoing teachings.

The invention claimed is:

1. An occluding device for occlusion of fluid flow through a lumen of a body vessel, the device comprising:
   a primary coil having primary coil windings forming a primary coil body with an outer primary coil radius and a primary coil lumen; and
   fibers attached to the primary coil, the fibers having a length extending generally radially across the primary coil body between the primary coil windings and outward therefrom, the fibers being blocked from slipping along their length relative to the coil body by an adhesive adhering to the fibers inside the primary coil lumen, the adhesive being limited to locations no farther outward than the outer primary coil radius.

2. The device of claim 1, wherein the adhesive is made of a durably elastic material.

3. The device of claim 1, wherein the adhesive joins a plurality of fiber strands into a fiber bundle.

4. The device of claim 3, wherein at least two fiber strands of the fiber bundle extend across the primary coil body between different axial coil windings.

5. The device of claim 1, wherein the adhesive thickens the fibers inside the primary coil lumen to a thickness greater than a distance between adjacent primary coil windings.

6. The device of claim 5, wherein the thickness is greater than the distance between adjacent coil windings when the primary coil is in a bent configuration.

7. The device of claim 6, wherein the primary coil has a relaxed shape that is curled into a secondary coil having a series of secondary loops, the thickness being greater than the distance between the adjacent coil windings when the primary coil is in its relaxed shape.

8. The device of claim 1, wherein the adhesive is made of a material that forms bonds with both the fibers and the primary coil windings.

9. An occluding device for occlusion of fluid flow through a lumen of a body vessel, the device comprising:
   a primary coil having primary coil windings forming a primary coil body with an outer primary coil radius and a primary coil lumen; and
   fibers attached to the primary coil, the fibers having a length extending generally radially across the primary coil body between the primary coil windings and outward therefrom, the fibers being blocked from slipping along their length relative to the coil body by an adhesive adhering to the fibers inside the primary coil lumen, the adhesive being limited to locations no farther outward than the outer primary coil radius, wherein the adhesive forms beads around the fibers.

10. An occluding device for occlusion of fluid flow through a lumen of a body vessel, the device comprising:
    a primary coil having primary coil windings forming a primary coil body with an outer primary coil radius and a primary coil lumen; and
    fibers attached to the primary coil, the fibers having a length extending generally radially across the primary coil body between the primary coil windings and outward therefrom, the fibers being blocked from slipping along their length relative to the coil body by an adhesive adhering to the fibers inside the primary coil lumen, the adhesive being limited to locations no farther outward than the outer primary coil radius, the adhesive joining a plurality of fiber strands into a fiber bundle and forming beads around the fibers.

11. The device of claim 10, wherein at least two fiber strands of the fiber bundle extend across the primary coil body between different axial coil windings.

12. An occluding device for occlusion of fluid flow through a lumen of a body vessel, the device comprising:
    a primary coil having primary coil windings forming a primary coil body with an outer primary coil radius and a primary coil lumen; and
    fibers attached to the primary coil, the fibers having a length extending generally radially across the primary coil body between the primary coil windings and outward therefrom, the fibers being blocked from slipping along their length relative to the coil body by an adhesive adhering to the fibers inside the primary coil lumen, the adhesive being limited to locations no farther outward than the outer primary coil radius, the adhesive forming beads around the fibers and thickening the fibers inside the primary coil lumen to a thickness greater than a distance between adjacent primary coil windings.

13. The device of claim 12, wherein the adhesive joins a plurality of fiber strands into a fiber bundle.

14. The device of claim 13, wherein at least two fiber strands of the fiber bundle extend across the primary coil body between different axial coil windings.

15. The device of claim 12, wherein the thickness is greater than the distance between adjacent coil windings when the primary coil is in a bent configuration.

16. The device of claim 15, wherein the primary coil has a relaxed shape that is curled into a secondary coil having a series of secondary loops, the thickness being greater than the distance between the adjacent coil windings when the primary coil is in its relaxed shape.

\* \* \* \* \*